United States Patent [19]

Schwartz

[11] Patent Number: 5,622,186
[45] Date of Patent: Apr. 22, 1997

[54] MALE ERECTION FACILITATION SHEATHS AND METHODS OF USE THEREOF

[76] Inventor: Alan N. Schwartz, 19211 - 93rd Place West, Edmonds, Wash. 98020

[21] Appl. No.: 609,947

[22] Filed: Mar. 4, 1996

Related U.S. Application Data

[63] Continuation-in-part of Ser. No. 912,683, Jul. 13, 1992, Pat. No. 5,513,652.

[51] Int. Cl.$^6$ ...................................... A61F 6/02
[52] U.S. Cl. .................... 128/842; 128/844; 600/38
[58] Field of Search ...................... 128/842, 844, 128/918; 604/347–353; 600/38–40

[56] References Cited

U.S. PATENT DOCUMENTS

| | | |
|---|---|---|
| 2,586,674 | 2/1952 | Lonne . |
| 4,798,600 | 1/1989 | Meadows . |
| 4,881,553 | 11/1989 | Grossman . |
| 4,919,149 | 4/1990 | Stang . |
| 4,987,905 | 1/1991 | Broad . |
| 5,027,802 | 7/1991 | Donohue . |
| 5,082,004 | 1/1992 | Reddy .................... 128/844 |
| 5,109,871 | 5/1992 | Thornton . |
| 5,111,831 | 5/1992 | Foggia .................... 128/844 |
| 5,121,755 | 6/1992 | Hegedusch . |
| 5,137,032 | 8/1992 | Harmon . |
| 5,284,158 | 2/1994 | Mallette .................... 128/918 |
| 5,331,974 | 7/1994 | Sook .................... 128/844 |
| 5,513,652 | 5/1996 | Schwartz . |

*Primary Examiner*—Michael A. Brown
*Attorney, Agent, or Firm*—Graybeal Haley Jackson LLP

[57] ABSTRACT

Prophylactic devices and methods for assisting in establishing and maintaining male erectile function. Open ended elastic sheaths with portions having different elasticity than have other portions, which portions of different elasticity cause selective constriction around and/or along selected portions of the penis by differential external pressures applied to said selected portions so as to not impede arterial blood flow to the penis but impede venous blood flow from the penis and thereby establish and maintain the penis in an erectile position. Various sheath configurations for the purpose include portions with lesser radius laterally of the longitudinal center axis of the sheath, or with more rigid portions, or with thicker portions, or with a balloon-like internal chamber fillable with a liquid or gas.

23 Claims, 2 Drawing Sheets

MALE ERECTION FACILITATION SHEATHS AND METHODS OF USE THEREOF

CROSS-REFERENCE TO RELATED APPLICATION

This application is a continuation-in-part of my application Ser. No. 07/912,683, entitled Male Erection Facilitation Sheaths and Methods of Using Same, filed Jul. 13, 1992, and which issued as U.S. Pat. No. 5,513,652 on May 7, 1996.

FIELD OF THE INVENTION

This invention pertains to devices for assisting erectile function and for prosthetic use, which need not interfere with circulation and interchange of bodily fluids during intercourse. More specifically, the present invention pertains to certain of such devices which are sheaths designed to exert different pressures on different portions of the male penis to facilitate erection, and to methods of use thereof.

SUMMARY OF THE INVENTION

Normal male erectile function requires numerous physiologic events to occur in concert. First, adequate neuropsychogenic, chemical or electrical stimulus must be present. Second, there must be adequate arterial blood inflow into the penis. Third, the corporal, smooth muscles must relax and corporal epithelial tissue must respond to the erectile stimulus, thus allowing the corporal sinusoids to expand and fill with blood. Finally, the venous closure mechanism must be initiated to prevent outflow of blood, thus resulting in storage of blood within the corpora cavernosum.

The penis is divided into four hydraulic chambers. Two corpora cavernosa straddles the corpus spongiosum. These chambers are crowned by the glans penis. The two corpora cavernosa are responsible for erection. Each corpora cavernosa is supplied by a cavernosal artery. The cavernosal artery flow and pressure determine the arterial competence of the erectile process. As the blood fills and expands these hydraulic chambers, the corporal venules and penile veins are compressed. This compression increases outflow resistance, permitting blood to flow into but not out of the corpora cavernosa. Intracorporal resistance is usually between about 5 to 10 mmHg×min/ml. Tumescence and rigidity result as blood is increasingly stored within the corpora cavernosa. Early in tumescence, intracorporal pressure is about 10 mmHg. During full tumescence, intracorporal pressure is between about 90 and 150 mmHg. Borderline erectile function is available at about 50 mmHg. Detumescence occurs when arterial inflow decreases, or corporal outflow increases, resulting in a net loss of blood from the penis. Some males are unable to obtain or sustain an adequate erection because sufficient intracorporal pressure cannot be achieved or maintained.

A need exists for a facilitator which is able to assist, in the case of borderline erectile function of about 50 mmHg intracorporal pressure for example, by applying localized external pressure onto the penis to produce an internal pressure change sufficient to increase the intracorporal pressure in the penis to a pressure well about 50 mmHg so that normal erectile function is achieved and maintained.

A need also exists for a facilitator for assisting erectile function in which pressure differential producing portions of the device, such as portions with woven strands, tapered portions, portions of lesser elasticity, thickened portions, and chambers containing solids or liquids, are variously employed to apply external pressure.

Facilitation sheaths of the present invention promote erections in a male suffering from borderline erectile failure caused by mild to moderate venous leakage or mild arterial incompetence with secondary venous leakage. When erectile failure occurs it can be the result of a venous leak (varicosity of the penis), inadequate arterial inflow volume and/or pressure, or neurological damage. Individuals with mild and moderate leaks, or with inadequate closure of the venous system, or inadequate arterial inflow can often achieve assisted erections. One known technique providing such assistance involves vacuum suction devices used to draw blood into the penis. This technique is predominately used to assist patients with arterial inadequacy by providing a pressure differential in the penis which is greater than the arterial pressure. Once blood is in the penis it is sequestered by placing a tight elastic band at the base of the penis. The suction devices operate on the concept that arterial inflow will be created by the section and the venous function if normal can maintain the erection. If the venous mechanism is not intact then the penis will leak through the tourniquet at the base of the penis.

Penile rings are used to prevent venous outflow. These are limited to constricting the outflow by compressing the penis at the base (downstream). This acts like a dam preventing the flow of blood out of the penis. This assists erections in some men with small leaks at the base of the penis, but the pressure is localized to the base. The constricting pressure often must exceed arterial pressure in order to effectively prevent the backed up venous blood from leaking out of the penis.

Sheath device of the present invention function in accordance with two major principles:

Firstly, venous leak out is more effectively impeded if the natural closure mechanism can be simulated and/or engaged at the site of the leak, rather than attempting to back up blood by placing a tourniquet downstream from the leak e.g. at the base of the penis.

In order to best impede the outflow of blood at the site of the leak, the resistance to outflow should occur at the site of the leak. This can be achieved by compression (external pressure) applied at the site of the leak.

Secondly, this compression should be dynamic not static. The compression pressure should increase with time, preferably in an exponential manner. That is, when the penis is partially tumesced (thickened) the pressure on the penis is to be localized to the site of the leak. Any portion of the penis which has achieved normal erection should not be exposed to undue external pressure early in the erectile process. The pressure to the abnormal (nonerectile) segments during early partial tumesce must be facilitated without being too severely constrictive. Pressure on the penis will increase with time as the penis expands, much like the force that would be exerted by a weightlifter if the weight he is lifting is increased exponentially over time. The initial resistance to the weight will be quite different from the final resistance. The lifter must adjust his resistance in response to the weight the lifter is resisting.

Selectively varying resistance and compression is the key to this invention. Prior art erection facilitators rely on fixed band-like constriction that exerts a compressive force that varies very little over time. With an erectile facilitation sheath of the invention, the compressive force adjusts and changes as the penis tumesces and elongates.

As in the well known Chinese finger puzzle, the penis elongates during tumesce. The penis also increases its circumference. The penile is restricted from expanding by the natural fascia of the penis. With the sheath the normal portions of the enlarging penile circumference are mildly restricted such that elongation occurs earlier than without the sheath. In turn, the abnormal portions are gently compressed early in erection, and this will slow the egress of blood out of the leaking portions of the penis. Without the sheath the damaged leaking areas would continue to leak and tumesce would not occur.

With the sheath in place the sheath becomes narrower at the sites which are normal. This shifts the blood to the sites of the venous leak. The areas of leak will then fill and tumesce. The portions that were previously narrow and unable to engorge and engage the venous closure mechanism, will initiate closure. This will promote the closure cycle. Tumescence, elongation and erection in sections that were previously incompetent because of leakage will now produce erections. The penis, even in damaged portions, can achieve closure of the exiting venules if tumesce (introcorporal-intrapenile pressure) can be sufficient to expand the sinusoids and squeeze the venules shut. There is of course a point where penile the damage is so severe that engagement of the biological closure mechanism is not possible. But in most individuals with early erectile failure the closure mechanism is partially functional and can be activated.

This invention allows men with early damage to the erectile mechanism to generate erections (introcorporal pressure levels between 70–100 mmHg) adequate for intromission (penetration), without the need for use of a vacuum suction device, penile injections, vasoactive medications, or prothesis.

These and other objects, features, and advantages of erection facilitation sheaths and methods of use thereof according to this invention will be apparent from the accompanying drawings and the following description of certain embodiments thereof.

BRIEF DESCRIPTION OF THE DRAWINGS

The foregoing objects and attendant features and advantages of this invention will become more readily appreciated as the same becomes better understood by reference to the following detailed description, taken in conjunction with the accompanying drawings, wherein.

DESCRIPTION OF THE PREFERRED EMBODIMENTS

Figure 1:
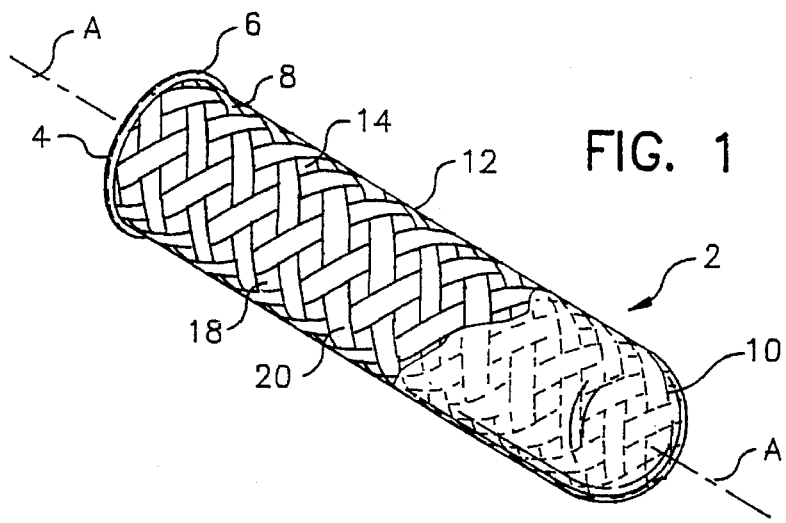
FIG. 1 is a perspective view of a first embodiment of the present invention, showing a first facilitator with a differential pressure generating weave pattern.
Figure 2:
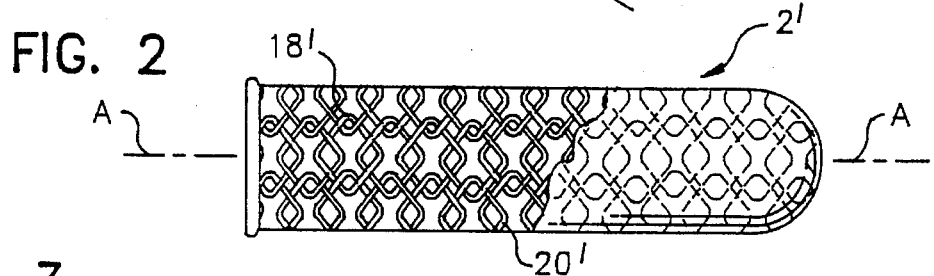
FIG. 2 is a plan view of the first embodiment of the present invention showing a second weave pattern.
Figure 3:
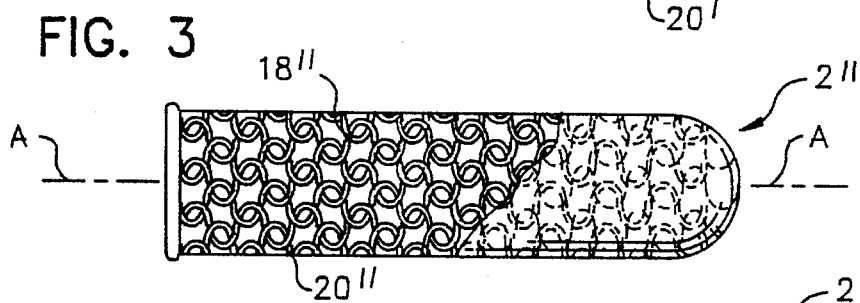
FIG. 3 is a plan view of the first embodiment of the present invention, showing a third weave pattern.

Referring to FIGS. 1–3, the erectile function facilitator there shown is preferably a sheath 2 having an open end 4 with a rim 6 circumferentially disposed therearound on base portion 8. Sheath 2 also has a closed tip portion 10, which may be open, and a central portion 12, as well as external surface 14 and internal surface 16 sheath 2 is concentric about a longitudinal center axis designated A, is preferably formed of latex, or of any other synthetic polymer or any other material employed for fabrication of prophylactics.

Open interwoven weave 18 is oriented over the surface of sheath 2. Weave 18 may either be integral with, or bonded to, the latex body of sheath 2. Weave 18 is comprised of a plurality of fibers 20 formed of latex or other fibrous synthetic or natural material. In FIG. 1, fibers 20 comprising weave 18 are interwoven both longitudinally on, and axially around facilitator 2. Thus, weave 18 maintains both elongation and expansion of an erect penis by constricting around and along the penis to impede venous blood flow therefrom. In such configuration, sheath 2 acts functionally much like the well-known Chinese finger puzzle.

Now referring to FIG. 2, the facilitator there shown is of the same construction as the facilitator shown in FIG. 1 except that weave 18 is comprised of fibers 20' which are interwoven only longitudinally on sleeve 2' such that weave 18' maintains elongation of an erect penis by constricting along the penis to impede venous blood flow therefrom.

In FIG. 3, the facilitator there shown is the same construction as the facilitator shown in FIG. 1 except that weave 18" has fibers 20" which are interwoven only axially around the facilitator 2". Thus, weave 18" maintains expansion of an erect penis by constricting around the penis to impede venous blood flow therefrom.

As shown in FIGS. 1–3, numerous different types of weaves 18, 18' and 18", for example, may be employed to maintain elongation and/or expansion of an erect penis. Specifically, the weave may be comprised of fibers such as 20, 20' and 20" which are linear, sinusoidal, interlocking squares, interlocking circles, as well as numerous other configurations so long as the fibers are interwoven longitudinally and/or axially around the sheath 2. The length of fibers on a given sheath is based upon the diameter of the flaccid penis such that the desired amount of constriction (external pressure) around and/or along the penis is imparted upon erection to impede venous blood outflow. The weave can cover either part or all of sheath, depending on the amount of constriction (external pressure) desired, and the specific location where the external pressure is applied. The specific location of the external pressure depends upon the location of penile vascular dysfunction.

Figure 4:
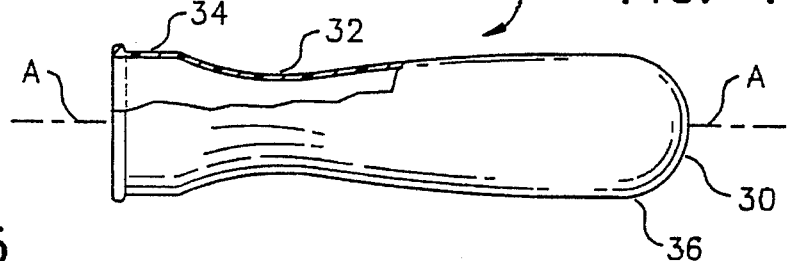
FIG. 4 is a plan view of a second embodiment of the present invention, showing a facilitator with a lesser cross-sectional diameter in the central portion of the facilitator.
Figure 5:
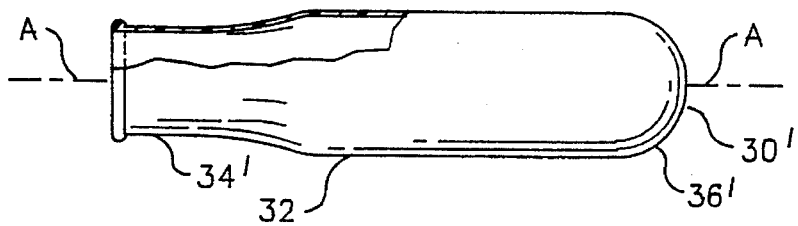
FIG. 5 is a plan view of the second embodiment of the present invention, showing a lesser cross-sectional diameter at the base portion of the facilitator.

FIGS. 4 and 5 disclose a second embodiment of the present invention in which the facilitator is configured so that the sheath has a smaller cross-sectional radius about its longitudinal center axis A in portions thereof than in other portions which in some instances facilitate erectile augmentation. In FIG. 4, for example, the sheath 30 is shown as having a reduced cross-sectional radius in the generally central portion 32 thereof as compared with the cross-sectional radius of the sheath 30 at the proximal and distal ends 34, 36 thereof. Similarly, as shown in FIG. 5, the sheath 30' there shown has a smaller cross-sectional radius in the proximal portion 34' thereof, as compared with the cross-sectional radius in the central and distal portions 32', 36' thereof. Similarly, as will be apparent, the reduced portion of lesser radius can be in any desired location such as in the distal end portion (not shown).

Figure 6:
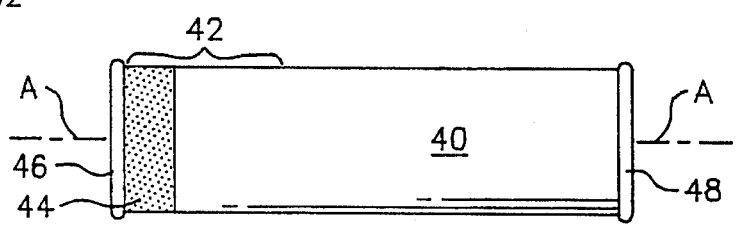
FIG. 6 is a plan view of a third embodiment of the present invention, showing a facilitator with a firmer band and consequently a lesser degree of elasticity at its base.

Referring now to FIG. 6, a third embodiment of the invention for assisting erectile function as shown in which the facilitator comprises a sheath 40 which has, circumferentially disposed around its base portion 42, a band 44 which is concentric about longitudinal axis A comprised of a material, such as a synthetic polymer, that has a degree of elasticity relatively less than the degree of elasticity over the remainder of sheath 40. In this manner, an erection is maintained by imparting an external pressure onto the penis to impede venous blood flow therefrom. Thus, as the penis becomes erect, the sheath 40 expands therewith, while band 44 expands to a lesser degree, or not at all, such that external pressure is induced. Band 44 may be integral with, or bonded to, sheath 40. The length and relative degree of elasticity of band 44 is determined by the relative diameter of the user's penis and the degree of external pressure desired to be imparted. While band 44 is shown around base portion 42, it can be located in any portion of sheath 40, and can cover any desired portion of the length or circumference of the sheath 40. Additionally, more than one band 44, interspaced by predetermined distances along the sheath, can be used.

The sheath shown in FIG. 6 also incorporates another variation which is applicable to all forms of sheath shown by the drawing. Specifically, this sheath 40 is open at both ends, with respective elastic end rings 46, 48.

Figure 7:
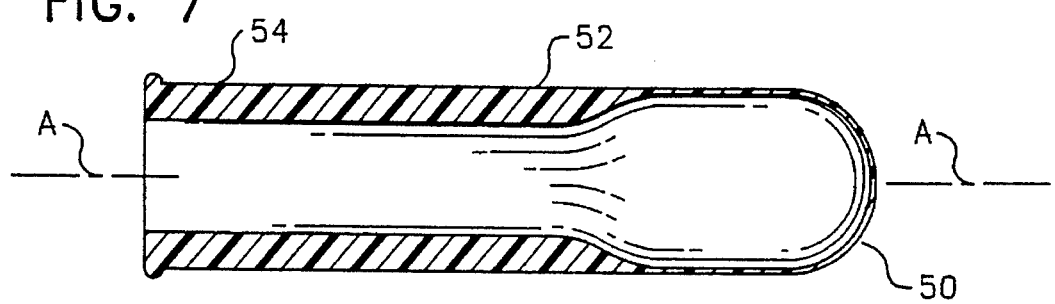
FIG. 7 is a cross-sectional view of a fourth embodiment of the present invention, taken along lines 7—7 of FIG. 6, and showing thicker central and base solid portions.

Referring now to FIGS. 7-13, a fourth embodiment of the invention for assisting erectile function is shown in which the facilitator comprises a sheath which also preferably functions as a prosthetic device for individuals who can only maintain a partial erection. Referring specifically to the form shown in FIG. 7, sheath 50 includes central and proximal thickened portions 52, 54 concentric about longitudinal axis A and having a thickness greater than that of the remainder of the sheath 50, preferably between about 2 and 15 mm, for example. In FIG. 7, thicker portions 52, 54 are solid and is preferably comprised of a synthetic polymer such as latex or silicone. The relatively greater depth of the thickened portions 52, 54 results in a degree of elasticity less than that of the remainder of the sheath 50 such that an erection is maintained by imparting an external pressure onto the central and rear portions of the penis to impede venous blood outflow. Additionally, the greater depth of thickened portions 52, 54 provides structural support of the penis for individuals who can only obtain partial erections. Thus, sheath 50 also functions as a prosthesis. The relative depth of thickened portions 52, 54 as well as the relative elasticity of thickened portions 52, 54 is determined by the relative diameter of the user's penis, the degree of external pressure desired to be imparted, as well as the amount of structural support desired.

Figure 8:
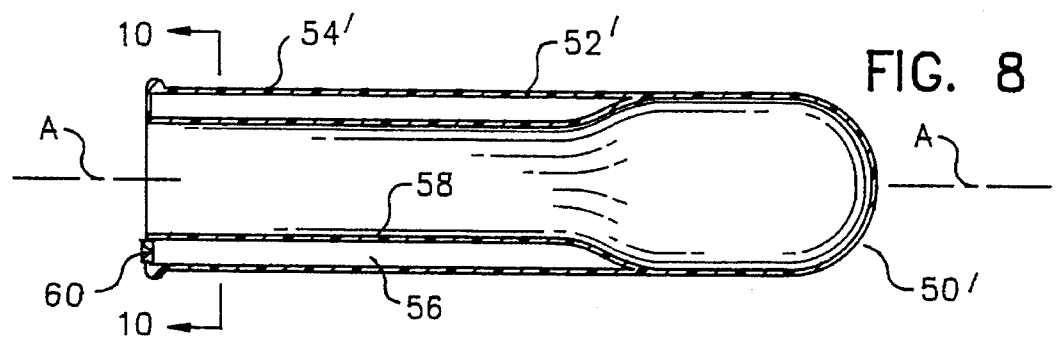
FIG. 8 is a cross-sectional view of the fourth embodiment of the present invention, taken at the same location on FIG. 6 as FIG. 7, and showing a double-walled, fluid-filled balloon portion centrally and at the base of the facilitator.

Referring now to FIG. 8, the fourth embodiment of the invention for assisting erectile function which also operates as a prosthetic device can, in the alternative, comprise a sheath 50' with thickened portions 52', 54' extending concentrically about longitudinal axis A, with internal chamber 56 therein. As opposed to the above described embodiment of FIG. 7 in which thickened portions 52, 54 are solid, FIG. 8 show thickened portions 52', 54' providing a chamber or balloon 56, with an inner wall 58, which is filled with a gas or liquid providing external pressure and support for the penis central and base portions. However, it is to be understood that a part of internal chamber 56 can be solid and a part can be gas or liquid filled.

Figure 9:
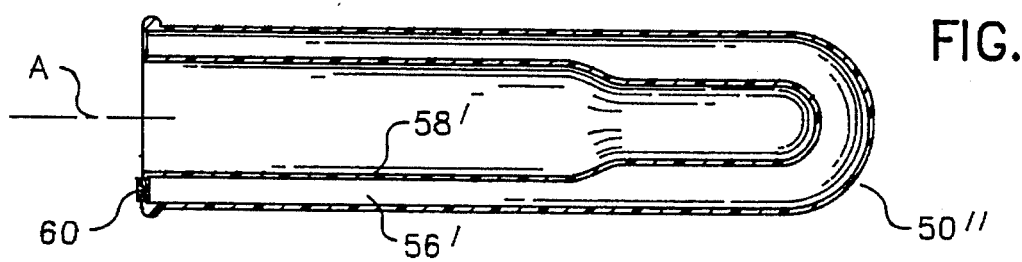
FIG. 9 is a cross-sectional view of the fourth embodiment of the present invention taken at the same location on FIG. 6 as FIG. 7 and showing a double-walled, fluid-filled balloon portion extending the entire length of the facilitator.
Figure 10:
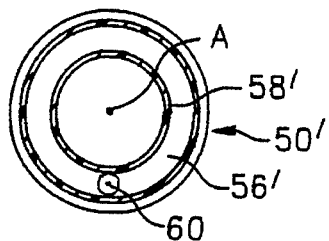
FIG. 10 is a cross-sectional view of the fourth embodiment of the present invention, taken along lines 10—10 of FIG. 8, and showing a first circumferential orientation of the balloon portion.

FIG. 9 shows a modified form of the form of sheath with a thickened wall in one or more portions. In it, the sheath 50" includes a chamber or balloon 56' which extends the full length of the sheath 50' and includes an inner wall 58' which also extends substantially the entire length of the sheath 50".

Figure 11:
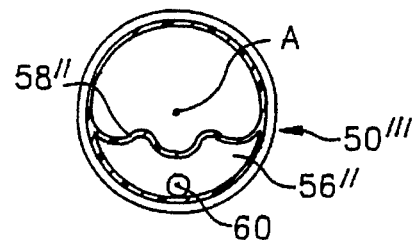
FIG. 11 is a cross-sectional view of the fourth embodiment of the present invention, taken at the same location on FIG. 8 as FIG. 10, and showing a second circumferential orientation of the balloon portion.
Figure 12:
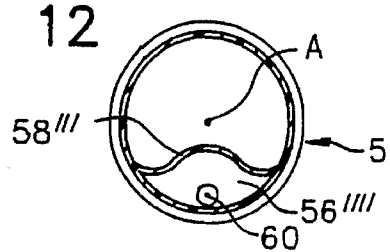
FIG. 12 is a cross-sectional view of the fourth embodiment of the present invention, taken at the same location on FIG. 8 as FIG. 10, and showing a third circumferential orientation of the balloon portion.
Figure 13:
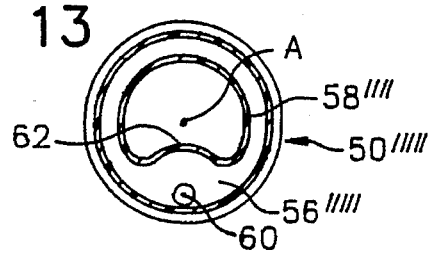
FIG. 13 is a cross-sectional view of a fourth embodiment of the present invention, taken at the same location on FIG. 8 as FIG. 10, and showing a fifth circumferential orientation of the balloon portion of the sheath.

FIGS. 10-13 are lateral cross-sectional views showing further variations in the configuration of the inner chamber or balloon of the sheath, such as taken along line 10—10 of FIG. 8. In the FIG. 10 form, there is included at the proximal end of the sheath a one-way valve 60 through which a gas or liquid can be admitted into the chamber or balloon 56. FIG. 11 shows another version of the internal balloon including a configuration characteristic of this embodiment, wherein the inner wall 58" provides a balloon or inner chamber 56" extending only partially around the sheath 50'", with the inner wall 58" nonconcentric relative to the longitudinal axis A. FIG. 12 shows yet another configuration with a nonconcentric inner wall 58'" which has a different cross-sectional contour than the inner wall 58" of the form shown in FIG. 11. FIG. 13 is another version of this embodiment, wherein the sheath 50"" includes an inner wall 58"" which defines a balloon 56"" extending fully circumferentially of the sheath thicker portions. Inner wall portion 62 thereof is nonconcentric relative to the longitudinal axis A. The thickened portion (56—56"") can be solid or fluid. When fluid, the gas or liquid is suitably admitted through valve means such as valve 60 utilizing the injection means known in the art. The gas can be air, and the liquid can be water, for example, and the amount of gas or liquid employed to fill the balloon or internal chamber is determined by the relative diameter of the user's penis, the degree of external pressure desired to be imparted to minimize venous leakage, the amount of structural support needed, and the location where the application of external pressure is needed. In general also, the thickened portion can laterally surround (FIGS. 10 and 13) or can extend only partly around (FIGS. 11 and 12) the sheath, and the inner surface of the sheath can be smooth and concentric (FIG. 10) or be nonconcentrically contoured to impart most efficiently the requisite external pressure at the site on the penis of the venous leak (FIGS. 11, 12 and 13). Additionally, the contour of the thickened portion may be such that the relative height of the thickened portion decreases or increases along the longitudinal axis.

While the foregoing embodiments and variations of the present invention are described individually can be combined to optimize the assistance of erectile Function and can be combined with other treatments or prophylaxis such as the dispensing of medicine, spermicide or bactricide as well as external layers or strips of hydrophobic or hydrophillic material.

While preferred embodiments of the invention have been illustrated and described, it will be appreciated that various changes and modifications can be made therein without departing from the spirit and scope of the invention as defined by the following claims.

What is claimed is:

1. The method of assisting in the establishment and maintenance of male penis erectile function, comprising:

selecting for installation on a flaccid or partially flaccid penis an erectile facilitator in the form of an elastic sheath open at both ends and of nominal size to realize in the penis when erect a selective differential pressure constriction around and/or along selected portions of the penis, said facilitator being characterized by having portions of different elasticity than the elasticity of the other portions thereof so as to be individually relatively movable in both longitudinal and circumferential directions in the sheath and consequently subject to elongation and/or expansion thereof to exert selective compression on selected portions of the penis responsive to relative increases in size of portions of the penis relative to other portions thereof;

installing said sheath on the flaccid or partially flaccid penis; and maintaining said sheath in position on the penis while maintaining arterial blood flow to the penis, with selective constrictions of selective portions of the penis by the sheath acting to not impede arterial blood flow to the penis but to impede venous blood flow from the penis and thereby enable the establishment and maintenance of the penis in an erectile condition.

2. The method of claim 1, comprising applying selective differential pressure to a portion of the penis not relatively as erectile as another portion thereof by engaging such less erectile penis portion with a portion of the sheath which is less elastic than the other portion thereof, with the result that greater external pressure is applied to said relatively less erectile penis portion than is applied to such other portion of the penis.

3. The method of claim 1, wherein said sheath portion having different elasticity than said other portion of the sheath are in lateral cross-section closer to the longitudinal axis of the sheath than are said other portion.

4. The method of claim 1, wherein said portion of the sheath of different elasticity than said other portion of the sheath are of a material characterized by greater resistance to enlargement than is said other portion of the sheath.

5. The method of claim 1, wherein said portion of the sheath having different elasticity than said other portion is characterized by a sheath wall of greater thickness than said other portion of the sheath has.

6. The method of claim 5, wherein the thicker portion of said sheath is concentric with the longitudinal center axis of the sheath.

7. The method of claim 1, wherein said portion of the sheath having different elasticity than said other portion is characterized by a lateral cross-section having an internal chamber fillable with a fluid to exert a differential external pressure on the portion of a wearer's penis in contact with said internal chamber than is exerted by said other portion of the sheath.

8. The method of claim 7, wherein said portion of said internal chamber of the sheath is nonconcentric relative to the longitudinal center axis of the sheath.

9. The method of claim 7, wherein said internal chamber of the sheath is in solid form.

10. A device for assisting in establishing and maintaining male erectile function comprising:

an elastic sheath open at both ends and adapted to fit onto a flaccid or partially flaccid penis; and said sheath having a portion of different elasticity than the elasticity of other portions thereof, the length and arrangement of said sheath portion of different elasticity being based on the diameter of the penis to realize in the penis when erectile a selective constriction around and/or along selected portions thereof so as to not impede arterial blood flow to the penis but to impede venous blood flow from the penis and thereby maintain the penis in an erectile condition.

11. A device according to claim 10, wherein said sheath portion having different elasticity than said other portions is in lateral cross-section closer to the longitudinal center axis of the sheath than are said other portions.

12. A device according to claim 10, wherein said portion of the sheath of different elasticity than said other portions is of a material characterized by greater resistance to increase in size than are said other portions of the sheath.

13. A device according to claim 10, wherein said portion of the sheath having a different elasticity than said other portions is characterized by a sheath wall of greater thickness than have said other portions of the sheath.

14. A device according to claim 13, wherein such thicker portion of said sheath is concentric with the longitudinal axis of the sheath.

15. A device according to claim 13, wherein such thicker portion of said sheath is nonconcentric relative to the longitudinal axis of the sheath.

16. A device according to claim 10, wherein said portion of the sheath having different elasticity than said other portions has a lateral cross-section closer to the longitudinal center axis of the sheath than are other portions of the sheath, with an internal chamber exerting a different external pressure on the portion of a wearer's penis in contact with said internal chamber than are exerted by said other portions of the sheath.

17. The method of claim 16, wherein said thicker portion of the sheath is in solid form.

18. The method of claim 16, wherein said thicker portion of the sheath is fillable with a fluid to exert such differential external pressure.

19. A device for assisting in establishing and maintaining male erectile function comprising:

an elastic sheath open at both ends and adapted to fit onto a flaccid or partially flaccid penis, said elastic sheath comprising a first portion of different elasticity than the elasticity of other portions thereof so as to permit said first portion to move relative to the other portions, the sheath causing in the penis when erectile a selective greater constriction around and/or along selected portions of the penis by differential external pressures applied to said selected portions of the penis by said first portion so as to not impede arterial blood flow to the penis but impede venous blood flow from the penis and thereby establish and maintain the penis in an erectile condition.

20. The method of assisting in the establishment and maintenance of male penis erectile function, comprising:

selecting for installation on a flaccid or partially flaccid penis an erectile facilitator in the form of an elastic sheath of nominal size to realize in the penis when erect a selective differential pressure constriction around and/or along selected portions of the penis, said facilitator being characterized by having a sheath wall portion forming an internal chamber of solid form concentric with the longitudinal center axis of the sheath and of different elasticity and greater thickness than the elasticity and wall thickness of other portions of the sheath so as to be individually relatively movable in both longitudinal and circumferential directions in the sheath and consequently subject to elongation and/or expansion thereof to exert selective compression on selected portions of the penis responsive to relative increases in size of portions of the penis relative to other portions thereof;

installing said sheath on the flaccid or partially flaccid penis; and maintaining said sheath in position on the penis while maintaining arterial blood flow to the penis, with selective constrictions of selective portions of the penis by the sheath acting to not impede arterial blood flow to the penis but to impede venous blood flow from the penis and thereby enable the establishment and maintenance of the penis in an erectile condition.

21. A device for assisting in establishing and maintaining male erectile function comprising:

an elastic open ended sheath adapted to fit onto a flaccid or partially flaccid penis; and said sheath having a portion of different elasticity than the elasticity of other portions thereof, with said sheath portion of different elasticity than said other portions being in lateral cross-section closer to the longitudinal center axis of the sheath than are said other portions, the length and arrangement of said sheath portion of different elasticity being based on the diameter of the penis to realize in the penis when erectile a selective constriction around and/or along selected portions thereof so as to not impede arterial blood flow to the penis but to impede venous blood flow from the penis and thereby maintain the penis in an erectile condition.

22. A device according to claim 21, wherein said portion of the sheath having a different elasticity than said other portions is characterized by having a sheath wall portion forming an internal chamber of greater thickness than have said other portions of the sheath, with such internal chamber thicker portion of said sheath being nonconcentric relative to the longitudinal axis of the sheath.

23. A device for assisting in establishing and maintaining male erectile function comprising:

an elastic open ended sheath adapted to fit onto a flaccid or partially flaccid penis; and said sheath having a portion of different elasticity than the elasticity of other portions thereof, the length and arrangement of said sheath portion of different elasticity being based on the diameter of the penis to realize in the penis when erectile a selective constriction around and/or along selected portions thereof so as to not impede arterial blood flow to the penis but to impede venous blood flow from the penis and thereby maintain the penis in an erectile condition, said portion of the sheath having different elasticity than said other portions having a lateral cross-section closer to the longitudinal center axis of the sheath than are other portions of the sheath, with an internal chamber of solid form exerting a different external pressure on the portion of a wearer's penis in contact with said internal chamber than are exerted by said other portions of the sheath.

\* \* \* \* \*